United States Patent [19]

Nakai

[11] Patent Number: 5,458,703
[45] Date of Patent: Oct. 17, 1995

[54] TOOL STEEL PRODUCTION METHOD

[75] Inventor: Norihiko Nakai, Shinminato, Japan

[73] Assignee: Nippon Koshuha Steel Co., Ltd., Tokyo, Japan

[21] Appl. No.: 110,925

[22] Filed: Aug. 24, 1993

Related U.S. Application Data

[63] Continuation-in-part of Ser. No. 813,652, Dec. 27, 1991, abandoned.

[30] Foreign Application Priority Data

Jun. 22, 1991 [JP] Japan .................................. 3-287364
Jun. 22, 1991 [JP] Japan .................................. 3-287365
Jun. 22, 1991 [JP] Japan .................................. 3-287366

[51] Int. Cl.[6] ............................................ C21D 9/00
[52] U.S. Cl. .................................. 148/503; 148/509
[58] Field of Search ............................ 148/503, 509

[56] References Cited

FOREIGN PATENT DOCUMENTS 352950  11/1972  U.S.S.R. ................................. 148/503
457743  1/1975   U.S.S.R. ................................. 148/503

*Primary Examiner*—Deborah Yee
*Attorney, Agent, or Firm*—Townsend & Banta

[57] ABSTRACT

A tool steel production method and a tool steel are disclosed in this invention. The method consists of following two steps:

1. Toughness (Ch) of the tool steel is evaluated from a formula:

$$Ch = f(Vp, H, T)$$

after estimating Vp, a square sum of output voltage of total Barkhausen noise signals which are produced in the process of magnetization of the tool steel sample, and measuring temperring hardness (H) and hardening temperature (T) of the tool steel sample.

2. A tool steel having a required toughness is produced by adjusting temperring hardness (H) and/or hardening temperature (T) based on the toughness evaluation of the tool steel sample mentioned above.

4 Claims, 3 Drawing Sheets

TOOL STEEL PRODUCTION METHOD

CROSS REFERENCE TO A RELATED APPLICATIONS

This is a continuation-in-part of application Ser. No. 07/813,652 filed Dec. 27, 1991, now abandoned.

FIELD OF THE INVENTION

This invention relates to a method for tool steel production and to the tool steel composition, and more particularly, to a production method for a tool steel with required toughness wherein the toughness of tool steel is estimated by using Barkhausen noise, tempering hardness and hardening temperature of tool steel, and to the tool steel produced by adopting the toughness estimation.

BACKGROUND OF THE INVENTION

Toughness is one of the characteristics to guarantee quality of a tool steel product. Toughness is the strength of a tool steel product against brittle fracture.

Brittleness breakage which has been known includes notch brittleness, temper brittleness, cold brittle fracture, etc. In order to guarantee the safety of a tool steel product, it is necessary to evaluate toughness of the product against them.

Parameters to evaluate the toughness include Charpy impact value ($kg.m/cm^2$), Izot impact value (ft.lb), absorbed energy, (upper) shelf energy, brittleness transition temperature (energy transition temperature, fracture transition temperature, 15ft-lb transition temperature, etc.), fracture toughness (plane strain fracture toughness value, energy release rate, elasticplastic fracture toughness value), etc.

In recent times hot metal molds used for hot working of metal material or the like, are getting larger and the environment in which they are used is getting severe. Under such circumstances, quality assurance of metal molds (hardness and toughness) after heat treatment has become significant. Specifically, if hardness and toughness of metal molds can be precisely evaluated non-destructively, it becomes possible to obtain both properties which conflict with each other, in optimum combinations, and quality assurance and long service life of metal molds can be achieved. At present, however, even though hardness is measured, there is no way available to non-destructively evaluate toughness. Therefore, insufficiency of toughness due to lowering of hardening and cooling velocity with enlargement of the metal mold cannot be accurately determined. This sometimes results in a large crack being formed at the beginning of use.

The present inventor has paid attention to Barkhausen noise (hereinafter called as "BHN") signals which can non-destructively detect any changes in composition sensitively because toughness of a metal mold is closely related to thermally treated composition Applicant also studied the relation among BHN signals standard value (hereinafter called as "dVp") of a square sum of output voltage of total BHN signals produced in the process of magnetization (hereinafter called as "Vp"), tempering hardness (hereinafter called as "It") and Charpy impact value (hereinafter called as "Ch") using a hardened and tempered material from standard hardening temperature (1020 ° C) of 0.4C-SCr-Mo-V hot metal mold steel, and reported a method to non-destructively evaluate toughness (Ch) of subject steel from a relational expression as Ch=f(dVp,H) ("Iron and Steel", 1990 (1989), Vol. 5, P. 833). According to this report, Ch is estimated by the following formula:

$$Ch = \delta_1 + \gamma_1 . H (kg.m/cm^2)$$

$$\delta_1 = a_1 + a_2.\log(a_3 + a_4.dVp)$$

$$\gamma_1 = b_1 + b_2.\log(a_3 + a_4.dVp)$$

$$a_3 = c_1 + c_2.H + c_3.H^2$$

$$a_4 = d_1 + d_2.H + k_3.H^2$$

$HRC43 \leq H \leq HRC51$ hardening temperature: 1020° C.

Ch of a tool steel which has been hardened and tempered from a hardening temperature of 1020° C. can be non-destructively evaluated from the above formula.

But, the actual hardening temperature of a metal mold is generally set at a level up to about 1015° C. when toughness is given priority and at a level up to about 1035° C. when strength is given priority. When the hardening temperature varies, the microstructure of a metal mold is different even when the tempering hardness (H) is same. Since toughness (Ch) is sensitive to microstructure, it is assumed that toughness (Ch) is different when the hardening temperature is different.

Therefore, when the hardening temperature is different from 1020° C., toughness (Ch) cannot be accurately assumed by using the relational expression of Ch-dVp-H, obtained from the aforementioned report of the Inventor. In order to assume Ch correctly, it is necessary to independently study the relation of Ch-dVp-H at various hardening temperatures.

SUMMARY OF THE INVENTION

This invention aims to provide a non-destructive evaluation method for toughness of tool steel having composition represented by following general formula:

$$C_a Si_b Mn_c Cr_d Mo_e W_f V_g Co_H Ni_i Nb_j Zr_k Cu_l Ti_m Ta_n B_o N_p Al_q P_r S_s Fe_{bal-ance}$$

and containing impurities which are unavoidably mingled (where, a:0.15–1.5(wt %, the same is applied hereinafter), b:2.5 or below, c:1.0 or below, d:0.4–21, e:5.0 or below, f:18 or below, g:3.0 or below, h:21.0 or below, 1:18.0 or below, j:1.25 or below, k:1.25 or below, 1:2.0 or below, m:2.5 or below, n:1.25 or below, o:0.010 or below, p:0.50 or below, q:1.20 or below, r:0.040 or below, and s:0.040 or below); by investigating the relation among BHN produced in the process of magnetization of tool steel, it's tempering hardness and hardening temperature, and expressing the relation as a formula.

In addition, this invention aims to provide tool steel having required toughness by using the above evaluation method in the process of tool steel production.

When analyzing BHN signals, a square sum of output voltage of total BHN signals produced In the process of magnetization (Vp) can be used.

As a representative amount of the aforementioned Vp, by utilizing a linear relation of Vp and maximum magnetizing voltage (hereinafter called as "Vm") and approximating their relation by the following formula:

$$Vp = Vp^* + b.Vm$$

virtual Vp value with Vm=OV (Vp*) can be used.

The above Vp* can be used as dVp standardized by the following formula:

$$dVp=\{(Vp^*)_I-(Vp^*)_A/(Vp^*)_B-(Vp^*)_A\}$$

where, (Vp*)$_A$: Vp* of standard material A, (Vp*)$_B$: Vp* of standard material B, (Vp*)$_I$: Vp* of each material I, and standard materials A, B: optional material that at least one of hardening temperature, hardening and cooling rates and tempering hardness is different.

DETAILED DESCRIPTION OF THE INVENTION

The relation among toughness of a tool steel, BHN produced in the process of tool steel magnetization, tempering hardness and hardening temperature in a temperature range broader than the practical hardening temperature range has been studied to clarify their relation in a practical hardening temperature range. Then the non-destructive evaluation method for toughness of tool steel by expressing toughness quantitatively and collectively in the form of a formula has been investigated.

For specifying BHN used in this invention, a parameter obtained based on total BHN signal output voltage (a square sum of output voltage of total BHN (Vp) and effective value (RMS) of a mean value of BHN output voltage), a parameter obtained based on instantaneous output voltage of BHN signals (maximum value of instantaneous output voltage (Vh) ) and a parameter obtained by frequency-analyzing of BHN (spectrum) which are produced in the magnetizing process can be used.

BHN is produced as concentrated in a certain time range (hereinafter called as "Δt") in the magnetizing process, and this production range (Δt) varies depending on magnetizing conditions and material (hardness, etc.) after heat treatment, even if the chemical components of tool steel are same. Therefore, to obtain RMS (a mean value of BHN output voltage) in Δt, it is necessary to fix Δt in advance. Besides, RMS depends on a way of fixing Δt.

On the other hand, as the above Vp is a square sum of total BHN output voltage in the magnetizing process, it is not necessary to fix Δt in advance. Therefore, as a BHN parameter, it is preferable to use Vp which is advantageous in mutually comparing the measured values obtained with different magnetizing conditions and different materials.

When Δt is too long to measure total BHN at a time in obtaining Vp, Vp can be obtained by dividing at into certain time periods, obtaining a square sum of BHN output voltage for the respective time range, and totaling the square sums.

Figure 5:
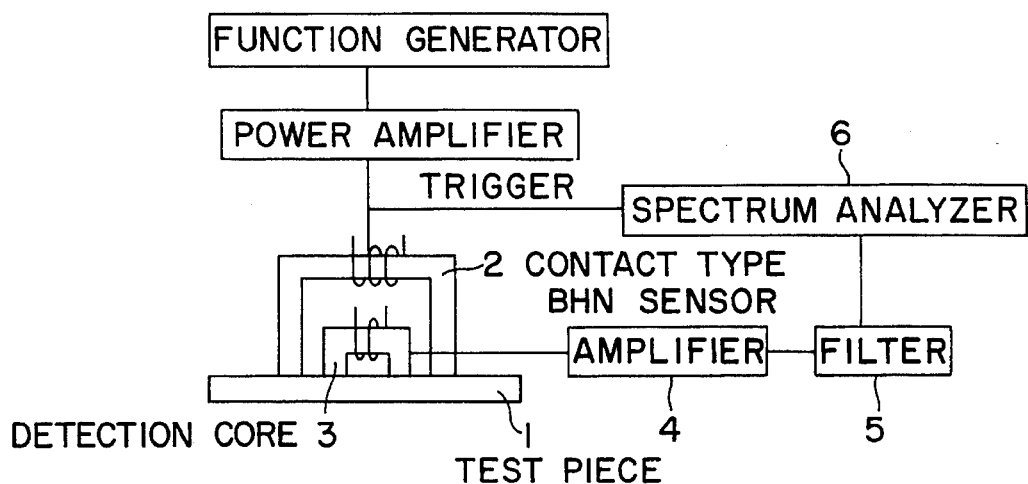
FIG. 5 is a schematic view showing the structure of Barkhausen noise measuring device used in one embodiment of this invention.

FIG. 5 shows conceptually the structure of BHN measuring device used in this embodiment. On a test piece 1, was disposed a contact type BHN sensor consisting of a magnetized core 2 which was made of Mn-Zn ferrite having a magnetized coil wound and a detection core 3 which was made of permalloy magnetic head having a detection coil wound. The detection coil wound on the above detection core 3 was connected to a spectrum analyzer 6 through an amplifier 4 and a filter (high-pass, low-pass) 5. For measuring BHN signals, test pieces are magnetized under a certain condition, generated induced electromotive voltage is detected with the detection core 3 and then BHN signals in the range of 700 to 10 kHz are analyzed with the spectrum analyzer 6.

Figure 1:
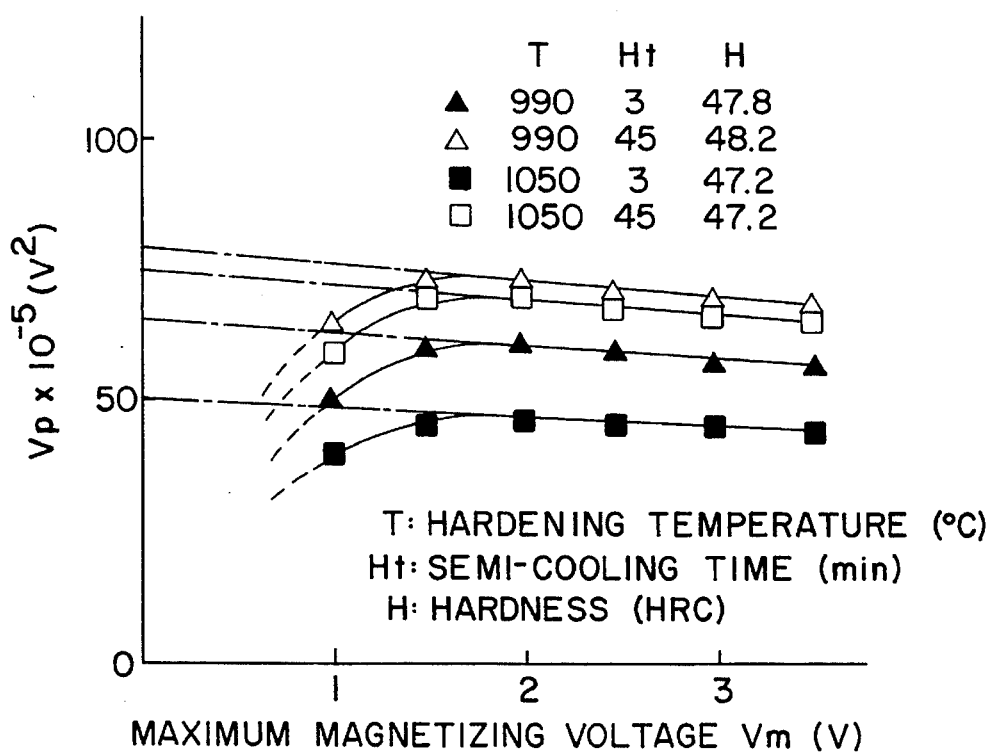
FIG. 1 is a graph showing dependence of a square sum of output voltage of total BHN signals (Vp) on maximum magnetizing voltage (Vm).

0.4C-5Cr-Mo-V steel having the chemical components given in Table 1 was thermally treated at hardening temperatures (T) of 990° C. and 1050° C., respectively with a hardening and cooling time or semi-cooling time (hereinafter called as "Ht") from the hardening temperature to 500° C. of 3 minutes and 45 minutes, respectively, and were magnetized under the condition indicated in Table 2. The relations between a square sum of output voltage of total BHN (Vp) and the maximum magnetizing voltage (Vm) of each material are shown in FIG. 1.

TABLE 1

| C | Si | Mn | Cr | Mo | V wt % |
|---|----|----|----|----|--------|
| 0.38 | 0.92 | 0.4 | 5.25 | 1.07 | 0.51 |

TABLE 2

| | |
|---|---|
| Magnetizing frequency | 1 Hz |
| Magnetizing voltage wave | Chopping wave |
| Maximum magnetizing voltage (V) | 1, 1.5, 2, 2.5, 3, 3.5 |

As shown in FIG. 1, all Vp sharply increases with the increase of Vm, and gradually lowers linearly after indicating the maximum value. Thus, as Vp depends on Vm, it is necessary to compare using Vp in the same Vm when mutually comparing the measured values of Vp for individual materials. In this case, a virtual Vp value in Vm=0(V) can be determined as a representative value (Vp*) of Vp by utilizing the linear relation of Vp with the Vm and approximating their relation by the following formula since Vp depends on Vm linearly as shown in FIG. 1.

$$Vp=Vp^*+b\cdot Vm$$

In addition, the aforementioned Vp* can be used as dVp standardized by the following formula:

$$dVp=\{(Vp^*)_I-(Vp^*)_A/(Vp^*)_B-(Vp^*)_A\} \quad (1)$$

where, (Vp*)$_A$: Vp* of standard material A, (Vp*)$_B$: Vp* of standard material B, (Vp*)$_I$: Vp* of each material I Thus, by standardizing Vp, material properties can be correctly evaluated even when the measured value of Vp* differs depending on the properties of a measuring device. As the standard materials A, B, an optional tool steel with at least one of hardening temperature (T), hardening and cooling rates (Ht) and temperring hardness (H) different can be used. For example, the standard materials A, B can be set as follows:

A:T=1020° C. Ht=3 min. H=HRC51.4
B:T=1020° C. Ht=3 min. H=HRC37.0

The aforementioned maximum value of instantaneous output voltage of BHN (Vh) can be obtained as follows.

BHN signals are repeatedly measured, each maximum value is obtained from the samples data of instantaneous output voltage, and a peak height of curves obtained by graduation treatment of the maximum values can be used as Vh. Vh thus obtained has better reproducibility than Vh which is a mean value obtained by repeatedly measuring BHN and simply averaging the maximum values of instantaneous output voltage for each measurement. Besides, the maximum value of amplitude of instantaneous output voltage of BHN or the maximum value of absolute values of instantaneous output voltage can be used as Vh.

0.4C-5Cr-Mo-V steel having the chemical components given in Table 1 was thermally treated at hardening temperatures (T) of 990° C. and 1050° C., respectively with a hardening and cooling time or semi-cooling time (tit) from the hardening temperature to 500° C. of 3 minutes and 45 minutes, respectively, and were magnetized under the condition Indicated in Table 2. The relations between the maximum value of instantaneous output voltage of BHN (Vh) and the maximum magnetizing voltage (Vm) of each material are shown in FIG. 2.

Figure 2:
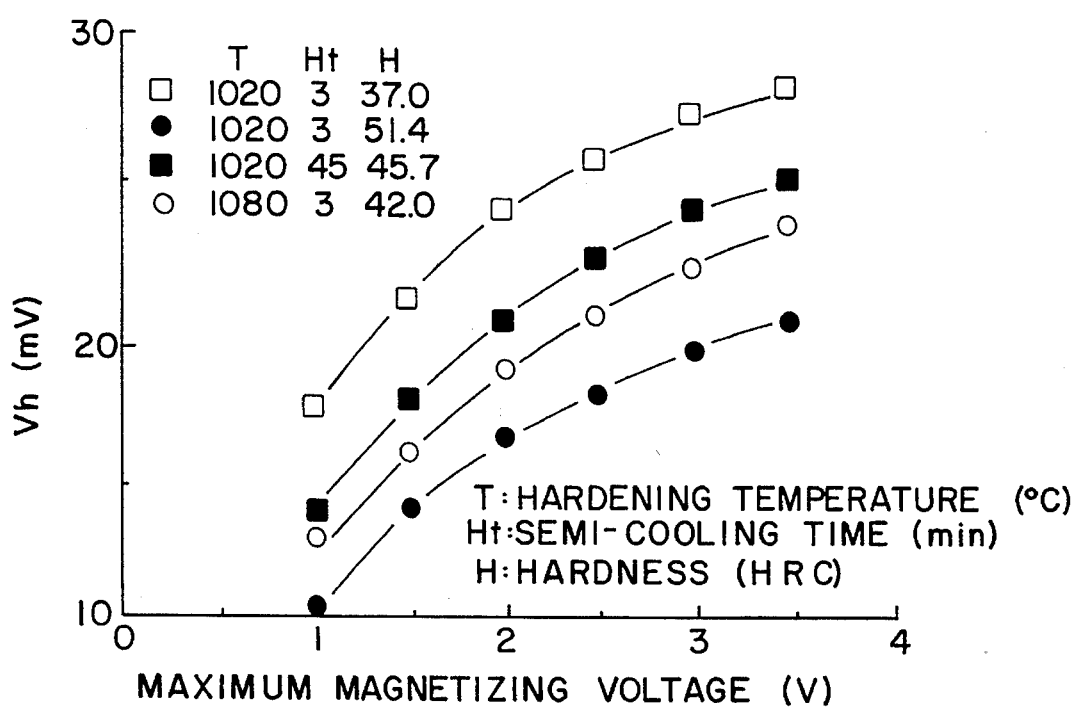
FIG. 2 is a graph showing dependence of maximum value of instantaneous output voltage of BHN signals (Vh) on Vm.

When mutually comparing the measured values for various tool steel, Vh in the same Vm has to be used for comparison as Vh depends on Vm as indicated in FIG. 2. In this case, each Vh-Vm curve is moved in parallel in the direction of Vh axis when its hardness varies and the distance between one Vh-Vm curve to another is constant without depending on Vm value. If standard material C is determined, parallel displacement distance (hereinafter called as "dVh*") in the direction of Vh axis required before Vh-Vm curve of standard material C and Vh-Vm curve of each material I are piled up can be obtained in the form of the following formula and Vh in the same Vm value can be used.

$$(dVh^*)I = \sum_{k-1}^{n} (Vh_{IK} - Vh_{CK})/n$$

where, n: level number of measured Vm, $Vh_{CK}$: Vh of standard material C in the Kth Vm, $Vh_{IK}$: Vh of material I in the Kth Vm, and optional material can be used as the standard material Co In addition, another standard material D is determined and the aforementioned dVh* can be used as dVh standardized by the following formula:

$$dVh = (dVh^*)_I/(dVk^*)_D$$

$$= \left\{ \sum_{k-1}^{n} (Vh_{IK} - Vh_{CK})/n \right\} / \left\{ \sum_{k-1}^{n} (Vh_{DK} - Vh_{CK})/n \right\}$$

As the standard material D, any optional material with at least one of hardening temperature, hardening and cooling rates and tempering hardness is different from that of standard material C can be selected.

Figure 3A:
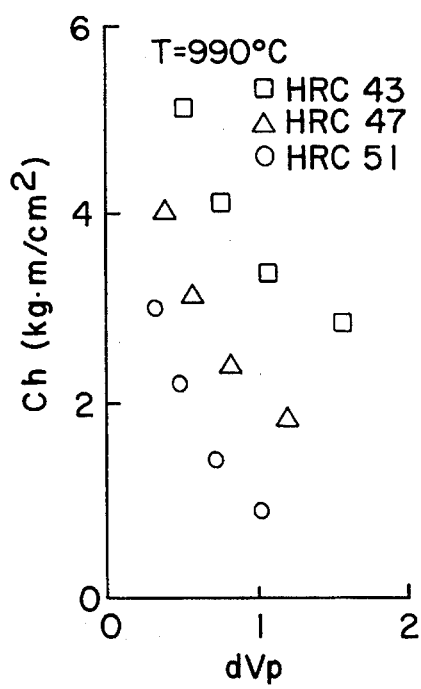
FIG. 3 is a graph showing dependence of Charpy impact value (Ch) on standardized value (dVp) of Vp.
Figure 3B:
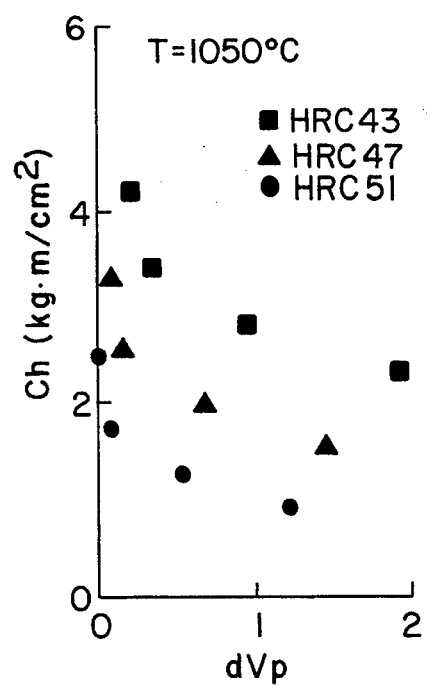
Figure 4:
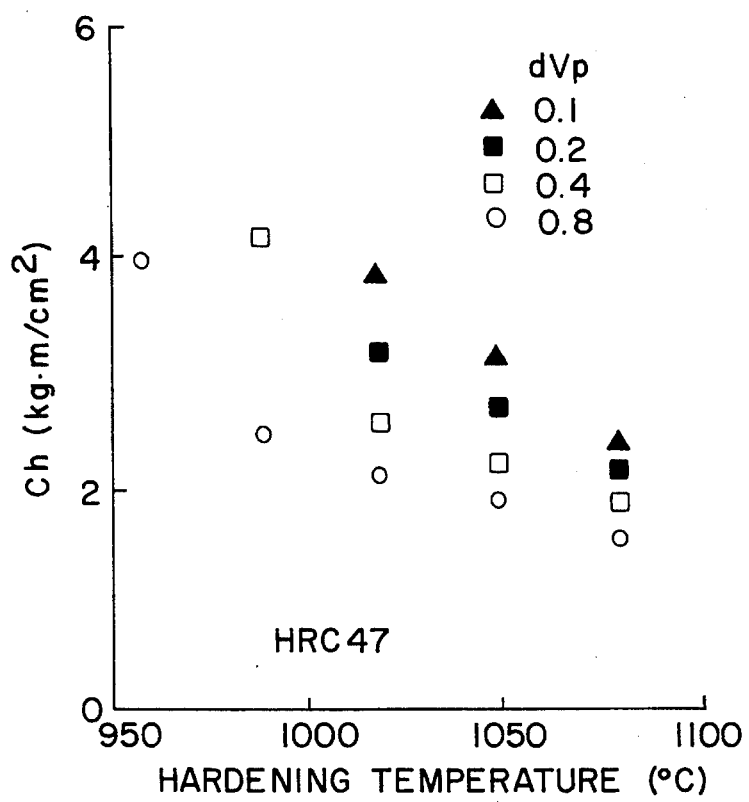
FIG. 4 is a graph showing dependence of Ch on hardening temperature (T).

FIG. 3 shows the relation among toughness (Ch) obtained by Charpy impact test, dVp and H of a tool steel hardened and tempered from T=990° C. and 1050° C. with respect to 0o4C-SCr-Mo-V steel with the chemical component shown in Table 1. As shown in FIG. 3, Ch depends on H and dVp qualitatively at either case of T=990° C. and 1050° C., and Ch lowers as H is larger or dVp is larger. The relation of dVp-H-Ch is qualitatively same with that of various values at T=1020° C. as already reported ("Iron and Steel" Vol. 75 (1989) No. 5, p.833–p.840) by the inventor. But, Ch not only depends on dVp and H but also on T as shown in FIG. 4. Therefore, to quantitatively obtain Ch at a temperature other than T=1020° C., it is necessary to clarify the comprehensive and quantitative relation of Ch-dVp-H-T containing T.

Test pieces with different hardening temperature, hardening and cooling rates and tempering hardness using materials shown in Table 1 were prepared, the aforementioned dVp and Ch were measured, and the comprehensive and quantitative relation of Ch-dVp-H-T in a temperature range broader than the actual hardening temperature range was studied by giving attention to the relation of Ch-T when dVp and H were made constant. As a result, it was found that the relation of Ch-dVp-H-T can be comprehensively and quantitatively in the form of functions of these various values as Ch=f(dVp, H, T).

According to the present invention, toughness (Ch) of a tool steel hardened and tempered from an ordinary hardening temperature can be evaluated non-destructively by measuring hardening temperature (T) and tempering hardness (H), estimating the above BHN parameter (dVp), and applying their various values to the function.

In addition, a tool steel having a required toughness can be produced by adjusting the production condition such as hardening temperature and tempering hardness based on the above evaluation.

Materials to which this invention is applied are those that the state of heat-treated composition affects on BHN, for example, tool steel such as SKD 5, SKD61, SKD62, SKD 7, SKD 8, etc. standardized by JIS (Japanese Industrial Standard). JIS standard mentioned above is correspond to AISI standard as follows:

| AISI | JIS |
|---|---|
| H21 | SKD5 |
| H13 | SKD61 |
| H12 | SKD62 |
| H10 | SKD7 |
| H19 | SKD8 |

Further, hardening temperature (T) of the subject tool steel when this invention is applied is not particularly defined. It is measured by a means for measuring, for example, a furnace atmospheric temperature with a thermocouple in order to evaluate austenitized state of the tool steel. But, in order to grasp the austenitized state more precisely, it is preferable to use a hardening parameter including not only a hardening temperature but also a retention time.

In addition, the method for measuring hardness in applying this invention is not particularly defined. Various hardness parameters such as "Brinell hardness", "Vickers hardness", "Knoop hardness", "Rockwell hardness", "Shore hardness", "Echochip hardness", etc. can be used. Hardness of the subject tool steel is not particularly restricted. For example, for hot metal mold, hardness is about HRC34 to HRC51 in Rockwell hardness, and for cold metal mold and high-speed steel, hardness may be about HRC70. For rotor material, hardness is lower than HRC43. In any case, this Invention can be applied to all these cases.

EXAMPLES

1. Material under test

Material under test is 0.4C-5Cr-Mo-V steel having the chemical components given in Table 1.

The above steel was molten in an arc type electric furnace and hot formed to a forging ratio of 6 or more, then annealed at 860° C. This test piece was collected in the forged elongation direction from the intermediate position of the center and corner and used in this invention.

2. Shape and heat treatment of test piece

BHN test piece and Charpy test piece were prepared as follows. BHN test piece had a size of 3mm×24mm×62mm and, after heat treatment, its surface was finished using abrasive paper No. 320. Charpy test piece had a depth of 2 mm and U-notch (R 1 mm). For heat treatment of the test pieces, with reference to the actually used heat treatment temperature of a metal mold, the test pieces were subjected to austenitizing treatment while keeping at T=960° C., 990° C., 1020° C., 1050° C. and 1080° C. for 30 minutes, then cooling time from the hardening temperature to 500 ° C. or Ht was selected to be four steps of 3 minutes, 15 minutes, 45 minutes and 110 minutes, uniform cooling was conducted by program control, and then temperring was conducted twice.

3. BHN measuring device, magnetizing condition and analyzing method

For measuring BHN signals, test pieces are magnetized under the condition indicated in Table 2. Using BHN measuring device shown in FIG. 5, generated induced electromotive voltage is detected with the detection core 3 and then BHN signals in the range of 700 to 10 kHz are analyzed with the spectrum analyzer 6 through an amplifier 4 and a filter (high-pass, low-pass) 5. Then Vp was adopted as BHN in this embodiment. First, the BHN generation time range (100 to 200 ms.) was divided into a time length (40 ms) capable of being measured at a time by the used device, the power values of BHN power spectrum were measured for respective time ranges, then they were totaled to obtain Vp. Then, standard dVp of Vp was obtained using the aforementioned formula (1).

4. Estimation of toughness (Charpy impact value: Ch)

With respect to each of test pieces, Hardness (H) was obtained, hardening temperature is determined with a furnace atmospheric temperature, Charpy test was conducted and dVp obtained above was used to Investigate the relation of Ch-dVp-H-T. As a result, the relation of Ch-dVp-H in a particular case of T=1020° C. which had been clarified could be indicated comprehensively and quantitatively as extended in the form, Ch= f(dVp, H, T) of a function containing T as shown in the following formula:

$$Ch = \delta_0 \delta_1 \cdot H (kg \cdot m/cm^2) \quad (2)$$

$$\delta_1 = a_1 + a_2 \cdot \log(a_3 + a_4 \cdot dVp)$$

$$a_1 = 16.6 - 0.377 \cdot (T-1020) - 5.21 \cdot 10^{-5} \cdot (T-1020)^2$$

$$a_2 = -2.14 - 0.0157 \cdot (T-1020) - 1.29 \cdot 10^{-5} \cdot (T-1020)^2$$

$$a_3 = c_1 + c_2 \cdot H + c_3 H^2$$

$$C_1 = -325 - 13.0 \cdot (T-1020) + 0.310(T-1020)^2$$

$$c_2 = 11.6 + 0.532 \cdot (T-1020) - 0.0123 \cdot T - 1020)^2$$

$$c_3 = -0.103 - 0.00503 \cdot (T-1020) + 0.000109 \cdot (T-1020)^2$$

$$a_4 = d_1 + d_2 \cdot H + d_3 \cdot H^2$$

$$d_1 = -440 + 10.2 \cdot (T-1020)$$

$$d_2 = 17.1 - 0.369 \cdot (T-1020)$$

$$d_3 = -0.0119 + 0.00292 \cdot (T-1020)$$

$$\gamma_1 = b_1 + b_2 \cdot \log(a_3 + a_4 \cdot dVp)$$

$$b_1 = -0.252 + 4.67 \cdot 10^{-4} \cdot (T-1020)$$

$$b_2 = -0.0171 + 4.20 \cdot 10^{-4} \cdot (T-1020)$$

where,
HRC43≦H≦HRC51, 990° C.≦T≦1050° C.

Figure 6:
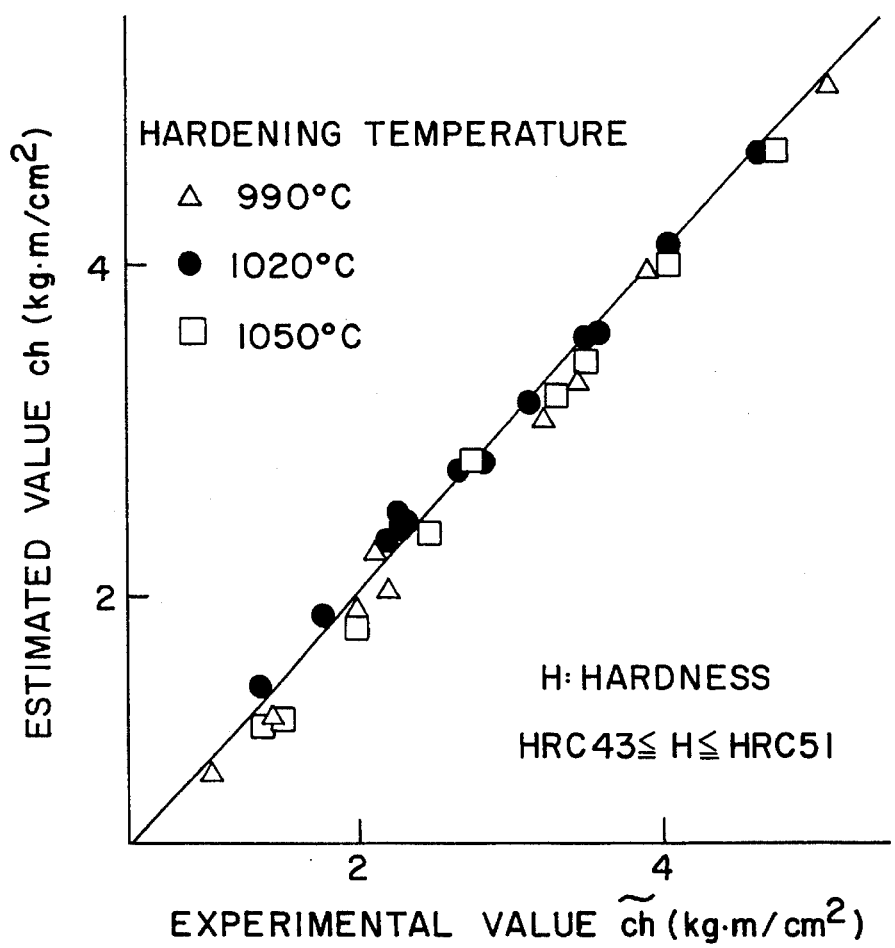
FIG. 6 is a graph showing results obtained by comparing estimates (Ch) which were obtained by using the non-destructive evaluation formula for toughness according to this invention with measured values (C̃h) which were obtained by experiments.

Estimated values (Ch) obtained by the formula (2) and measured values (C̃h) obtained by the Charpy test were compared and the result is shown in FIG. 6. As shown in FIG. 6, the estimated values and the measured values substantially agree. Therefore, H and T were measured, and dVp was obtained by using BHN, then these various values were applied to the formula (2), so that Ch could be comprehensively and quantitatively evaluated non-destructively in a normal hardening temperature range (1015° to 1035° C).

In addition, a tool steel having a required toughness can be produced by controlling tempering hardness (H) and hardening temperature (A) based on the estimation by the above formula (2).

This example shows the results on a Charpy impact value (Ch) at room temperature, but even in a temperature range of room temperature or above to 550° C., the relational expression of Ch-V-H-T can be formed in a shape different from the above example, and in this case, toughness can be evaluated non-destructively according to this invention and the required tool steel can be produced by using the obtained evaluation and controlling the production condition.

What is claimed is:

1. A method of producing a tool steel being hardened and tempered, having a toughness value (Ch) and comprising:

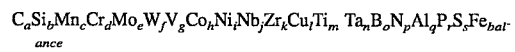

$$C_a Si_b Mn_c Cr_d Mo_e W_f V_g Co_h Ni_i Nb_j Zr_k Cu_l Ti_m\ Ta_n B_o N_p Al_q P_r S_s Fe_{balance}$$

(where, a:0.15-1.5 (wt %, the same is applied hereinafter), b:2.5 or below, c:1.0 or below, d:0.4–21, e:5.0 or below, f:18 or below, g:3.0 or below, h:21.0 or below, i:18.0 or below, j:1.25 or below, k:1.25 or below, 1:2.0 or below, m:2.5 or below, n:1.25 or below, o:0.010 or below, p:0.50 or below, q:1.20 or below, r:0.040 or below, and s:0.040 or below);

wherein toughness value is obtained by the steps comprising:

preparing a sample of objective tool steel and temper hardening said sample;

measuring tempering hardness (H) of the sample;

measuring hardening temperature (T) of the sample;

magnetizing the sample of the tool steel;

measuring an output voltage of total BHN across the sample in the process of magnetizing and estimating a value (Vp) by adding each square sum of output voltage of total BHN;

measuring the toughness value (Ch) of the sample by Charpy impact test;

obtaining a functional formula: Ch=f(Vp, H, T) from the measured values;

measuring each value of (Vp), (H), and (T) of the tool steel in an actual production process; and estimating the toughness value (Ch) of the tool steel by substituting measured values of (Vp), (H) and (T) of the tool steel into functional formula: Ch=f(Vp, H, T).

2. A method of producing a tool steel being hardened and tempered, having a toughness value (CH) and comprising:

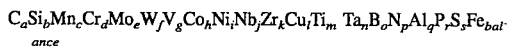

(where, a:0.15–1.5 (wt %, the same is applied hereinafter), b:2.5 or below, c:1.0 or below, d:0.4–21, e:5.0 or below, f:18 or below, g:3.0 or below, h:21.0 or below, i:18.0 or below, j:1.25 or below, k:1.25 or below, 1:2.0 or below, m:2.5 or below, n:1.25 or below, o:0.010 or below, p:0.50 or below, q:1.20 or below, r:0.040 or below, and s:0.040 or below);

wherein toughness value is obtained by the steps comprising:

preparing a sample of objective tool steel and temper hardening said sample;

measuring tempering hardness (H) of the sample;

measuring hardening temperature (T) of the sample;

magnetizing the sample of the tool steel;

measuring a maximum value (Vh) of instantaneous output voltage of total BHN across the tool steel in the process of magnetization;

measuring a toughness value (Ch) of the sample by Charpy impact test;

obtaining a functional formula: Ch=f(Vh, H, T) from the measured values;

measuring each value of (Vh), (H) and (T) of the tool steel in the actual production process; and estimating the toughness value (Ch) of the tool steel by substituting measured values of (Vh), (H) and (T) of the tool steel into functional formula: Ch=f(Vh, H, T).

3. The method according to claim 1, wherein the value (Vp) of the sample is obtained by the steps comprising:

measuring and estimating each (Vp) value of the sample when the maximum magnetizing voltage (Vm) is varied;

obtaining a functional formula: Vp=b.Vm by approximating a linear relation between (Vp) and (Vm);

estimating a virtual Vp value (Vp*) in Vm=OV using functional formula: Vp=b.Vm; and obtaining (Vp) value by a formula: Vp=Vp*+b.Vm.

4. The method according to claim 3, wherein the value (Vp) is obtained as (dVp) which is a standardized value of (Vp) by the following formula:

$$dVp=\{(Vp^*)_I-(Vp^*)_A/(Vp^*)_B-(Vp^*)_A$$

wherein, $(Vp^*)_A$: Vp* of standard material A, $(Vp^*)_B$: Vp* of standard material B, $(Vp^*)_I$: Vp* of each material I, and standard materials A, B: optional material that at least one of hardening temperature, hardening and cooling rates and tempering hardness is different.

* * * * *